United States Patent [19]

Krapcho

[11] Patent Number: 4,963,671
[45] Date of Patent: Oct. 16, 1990

[54] PROCESS FOR RESOLVING CHIRAL INTERMEDIATES USED IN MAKING CALCIUM CHANNEL BLOCKERS

[75] Inventor: John Krapcho, Somerset, N.J.

[73] Assignee: E. R. Squibb & Sons, Inc., Princeton, N.J.

[21] Appl. No.: 438,136

[22] Filed: Nov. 20, 1989

[51] Int. Cl.$^5$ .......................................... C07D 281/10
[52] U.S. Cl. ...................... 540/491; 510/17; 562/431
[58] Field of Search .......... 540/491; 560/17; 562/431

[56] References Cited

U.S. PATENT DOCUMENTS 3,562,257  2/1971  Kugita et al. .................. 540/491

OTHER PUBLICATIONS

Kugita et al., "Synthesis of 1,5-Benzothiazepine Derivatives", I Chem. Pharm. Bull. vol. 19 pp. 2028 to 2037 (1970).

Primary Examiner—Robert T. Bond
Attorney, Agent, or Firm—Donald J. Barrack; Timothy J. Gaul

[57] ABSTRACT

This process enables preparation of the preferred (+)-threo enantiomer by resolution of its racemic mixture of a compound of the formula

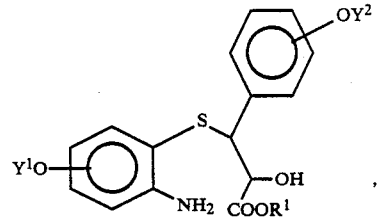

wherein $Y^1$ and $Y^2$ are each independently lower alkyl and $R^1$ is hydrogen or lower alkyl. The compound is treated with a chiral acid (tartaric aicd preferred) in an organic solvent (ethanol preferred) to yield the (+)-threo enantiomer, which is then recovered from the reaction mixture. This enantiomer may then be used to produce the preferred (+)-cis enantiomer of certain benzothiazepine cardiovascular agents.

14 Claims, No Drawings

PROCESS FOR RESOLVING CHIRAL INTERMEDIATES USED IN MAKING CALCIUM CHANNEL BLOCKERS

FIELD OF THE INVENTION

This invention relates to a process for preparing the (+)-threo and (+)-cis isomers of certain intermediates useful in making calcium channel blocking cardiovascular agents.

BACKGROUND OF THE INVENTION

U.S. patent application Ser. No. 353,806, filed May 22, 1989, now U.S. Pat. No. 4,902,884, describes compounds of the formula

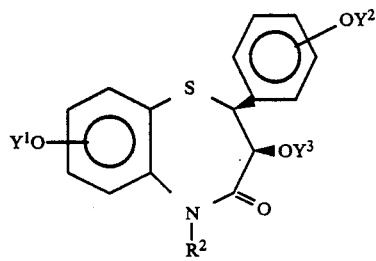

and the pharmaceutically salts thereof, which are calcium channel blockers and thus possess useful vasodilating activity and may be used as antihypertensive agents. In formula I and throughout this specification, the symbols are defined as follows:

$R^2$ is

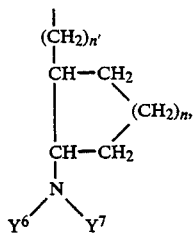

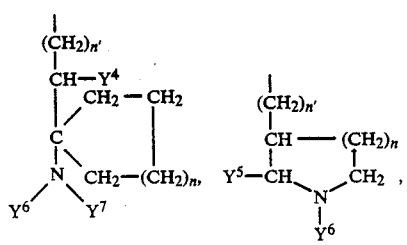

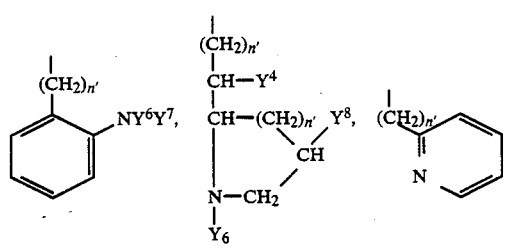

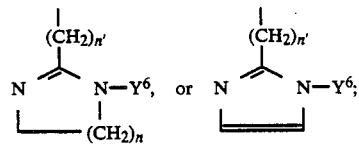

$Y^1$ is lower alkyl;
$Y^2$ is lower alkyl;
$Y^3$ is hydrogen, alkyl, alkenyl,

or

$Y^4$ and $Y^5$ are each independently hydrogen, alkyl, aryl or arylalkyl, provided that when both are present they are not both hydrogen, and provided further that when both are attached to the same carbon atom neither of them is hydrogen;

$Y^6$ and $Y^7$ are each independently hydrogen, alkyl, cycloalkyl or arylalkyl; or $Y^6$ and $Y^7$ together with the nitrogen atom to which they are attached are azetidinyl, pyrrolidinyl, piperidinyl, or morpholinyl;

$Y^8$ is hydrogen, hydroxy, alkoxy, aryloxy, or arylalkoxy;

$Y^9$ and are each independently hydrogen, alkyl, aryl, or heteroaryl, or $Y^9$ and $Y^{10}$ together with the nitrogen atom to which they are attached are pyrrolidinyl, piperidinyl, or morpholinyl;

n is 0, 1, 2, or 3; and
n' is 0, 1, 2, or 3.

Exemplary formula I compounds are the compound having the structure

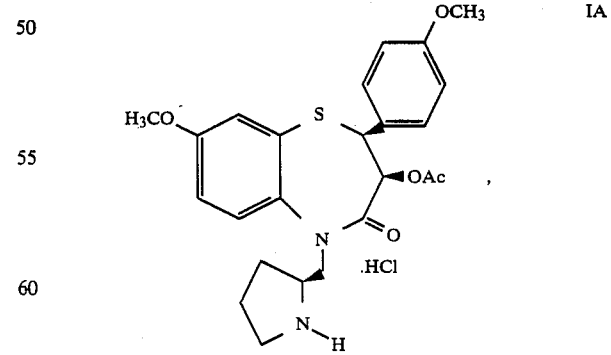

and the name [2S-[2α,3α,5α,5(R*)]]-3-(acetyloxy)-2,3-dihydro-S-methoxy-2-(4-methoxyphenyl)-5-(2-pyrrolidinylmethyl)-1,5-benzothiazepin-4(5H)-one, and the compound having the structure

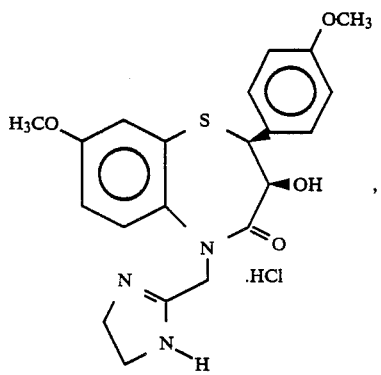

IB

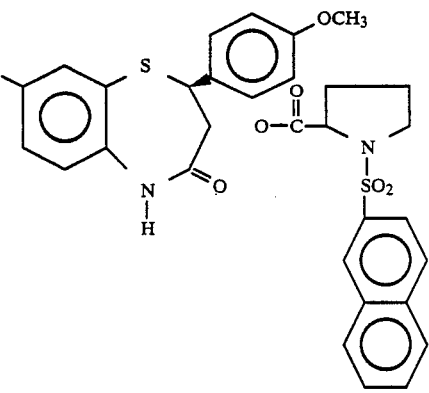

C.

and the name (2S-cis)-5-[(4,5-dihydro-1H-imidazol-2-yl)methyl]-2,3-dihydro-3-hydroxy-8-methoxy-2-(4-methoxyphenyl)-1,5-benzothiazepin-4(5H)-one, monohydrochloride.

U.S. application Ser. No. 353,806, now U.S. Pat. No. 4,902,684, also indicates that the carbon atoms in the 2 and 3-positions of the benzothiazepine nucleus of the compounds of formula I are asymmetric carbons and, therefore, such compounds exist in enantiomeric and diastereomeric forms and as racemic mixtures thereof. This application also indicates that those compounds of formula I which have the cis configuration are the most potent and are therefore preferred.

According to U.S. patent application Ser. No. 353,806, now U.S. Pat. No. 4,902,684, compound I in (+)-cis form may be prepared by reacting the known racemic benzothiazepine intermediate

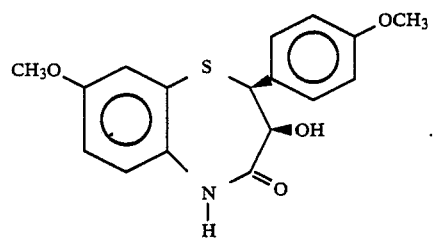

A.

with a nonracemic acid or amino acid

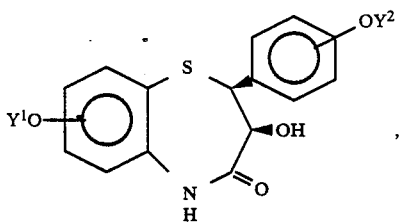

B.

wherein Z and $Z_1$ are different, using a conventional esterifying agent (e.g., carbodiimide) with a catalyst (e.g., 4-dimethylaminopyridine) to give a mixture of diastereomers separable by conventional techniques.

In European patent application No. 154,838, the benzothiazepine is prepared and the isomers separated by crystallization and chromatography and then hydrolyzed to isolate the (+) isomer compound

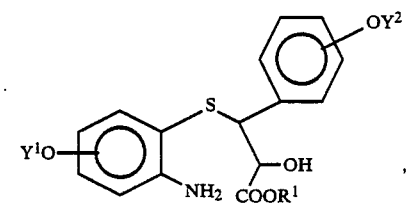

D.

The art would benefit from a procedure by which the preferred isomeric configuration could be produced earlier in the preparation of the benzothiazepines, thus maximizing yields of the preferred enantiomer of the benzothiazepine cardiovascular agents.

BRIEF DESCRIPTION OF THE INVENTION

In accordance with the present invention, a process is provided for resolving the threo isomer of a compound of the formula II

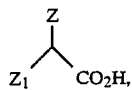

II to give exclusively the (+)-threo form, wherein:
 $Y^1$ is lower alkyl, preferably methyl;
 $Y^2$ is lower alkyl, preferably methyl;
 $R^1$ is hydrogen or lower alkyl and preferably is methyl;
and wherein a racemic mixture of a compound of formula II is treated with a chiral acid (tartaric acid preferred) in an organic solvent (ethanol preferred) and the (+)-threo isomer is recovered therefrom. Compound II is an intermediate that may be used to prepare compounds of formula I. The (+)-threo isomer of compound II is especially useful in preparing the preferred (+)-cis isomer of compound I.

Also in accordance with the present invention, a process is provided for hydrolyzing the (+)-threo isomer of compound II to provide the amino acid

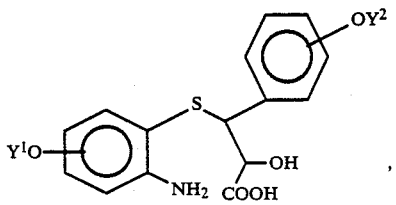

III followed by cyclization to give the (+)-cis isomer of the compound

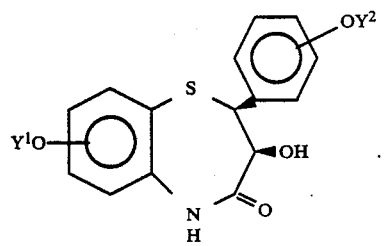

IV

Further in accordance with the present invention, there is provided processes for preparation of the preferred (+)-cis isomer of compounds of formula I using the (+)-cis intermediate II.

The processes of this invention resolve to the preferred (+) isomer much earlier in the preparation than was known in the prior art. The present processes have the advantages of being considerably more efficient and less expensive.

DETAILED DESCRIPTION OF THE INVENTION

Listed below are definitions of various terms used to describe this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred. The terms "lower alkyl" and "lower alkoxy", however, refer to straight and branched chain groups having 1 to 4 carbon atoms.

The term "alkenyl" refers to both straight and branched chain groups. Those groups having 2 to 10 carbon atoms are preferred.

The term "aryl" refers to phenyl and substituted phenyl. Exemplary substituted phenyl groups are phenyl groups substituted with 1, 2 or 3 amino (—NH$_2$), alkylamino, dialkylamino, nitro, halogen, hydroxyl, trifluoromethyl, lower alkyl, lower alkoxy, alkylthio (of 1 to 4 carbon atoms), alkanoyloxy (of 2 to 4 carbon atoms) carbonyl, or carboxyl groups.

The term "cycloalkyl" refers to groups having 3, 4, 5, 6 or 7 carbon atoms.

The process of the present invention begins with a racemic mixture of compound II (disclosed in European Patent Application No. 154,838, filed Feb. 15, 1985). Compound II is treated with a chiral acid such as tartaric acid in an organic solvent, at a temperature of about 50° to 80° C. in molar ratios from about 1.0:1.1 to about 1.0:1.5 compound II:chiral acid and about 1:10 compound II: organic solvent to resolve the (+)-threo isomer of compound II, which may be recovered from the mixture. Other chiral acids are useful for this process, including camphoric and camphorsulfonic acid (see Newman, *Optical Resolution Procedures, Volume I: Amines and Related Compounds*, pp. 7 to 24 (1978)). The organic solvent may be ethanol, isopropyl alcohol, aqueous ethanol, methanol, acetone, ethyl acetate, butanol, and the like. Alcohol solvents, particularly ethanol and 95% ethanol, are preferred. The moieties —OY$^1$ and —OY$^2$ in compound II are preferred to be attached so that compound II follows the more specific formula

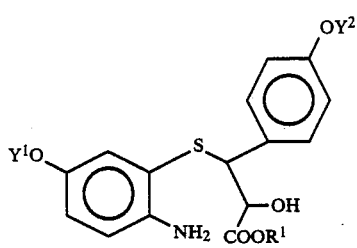

IIA

The resolved (+)-threo intermediate compound II may be used to prepare final products I and intermediates thereof in preferred (+) form as described below.

In accordance with the present invention, resolved (+)-threo isomer of compound II is hydrolyzed with an aqueous alkali hydroxide (e.g., sodium hydroxide) in an organic solvent (e.g., methanol) at a temperature of about 10° to 40° C. to yield the (+)-threo isomer of compound III.

Further to this invention, compound III is reacted with an aqueous solution of ethyl-3-(3-dimethylamino)-propyl carbodiimide, hydrochloride (WSC) in an organic solvent (e.g., dimethylformamide), present in a molar ratio from about 1:1 to about 1:1.7 compound III:WSC, at a temperature of about 20° to 40° C. to yield the (+)-cis compound IV.

Further to this invention, the corresponding (+)-cis compound of formula I may be obtained by treatment of compound IV with a base (e.g., sodium hydride or cesium carbonate) in an inert solvent (e.g., dimethylformamide or dimethylsulfoxide), present in a molar ratio of about 1:2 compound IV: base and at a temperature of about 20° to 70° C., followed by reaction with a compound of the formula $$R^2-L \qquad V$$

(wherein L is a leaving group such as halo or tosyloxy), present in a molar ratio of about 1:2 compound IV:compound V and at a temperature of about 20° to 70° C.

Alternatively, in accordance with the present invention, a compound of formula I in (+)-cis form can be prepared by reacting compound IV with compound V under phase transfer conditions in a mixture of water and dichloromethane or toluene in the presence of an appropriate base (e.g., barium hydroxide or sodium hydroxide) and a catalyst (e.g., benzyl trimethylammonium chloride or tetra-n-butylammonium hydrogen sulfate), in a molar ratio from about 1:1 to about 1:1.5 compound IV:compound V and at a temperature of about 20° to 70° C.

Alternatively, in accordance with the present invention, the products of formula I in (+)-cis form wherein

7

Y³ is hydrogen can be acylated with an acylating agent (e.g., acetic anhydride) present in a molar ratio from about 1:3 to about 1:10 compound I:acylating agent at a temperature of about 20° to 40° C. to obtain those cis products of formula I wherein Y³ is

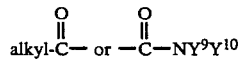

(preferably acetyl).

The following examples are specific embodiments of this invention and are meant to be illustrative rather than limiting. Except where otherwise indicated, all temperatures are in degrees Celsius.

EXAMPLE 1

(+)-Threo-2-hydroxy-3-(2-amino-5-methoxyphenylthio)-3-(4-methoxyphenyl)propionic acid, methyl ester, salt with D-(−) tartaric acid 1-A. (±)-Threo-2-hydroxy-3-(2-amino-5-methoxyphenylthio)-3-(4-methoxyphenyl) propionic acid, methyl ester To a 2-liter, 3-necked flask equipped with a magnetic stirrer, condenser and a gas inlet tube was added 50.5 g (0.243 mol) of (trans)-3-(4-methoxyphenyl) oxirane carboxylic acid, methyl ester, 42.9 g (0.276 mol) of 2-amino-5-methoxythiophenol and 300 ml of toluene. Nitrogen was passed over this suspension and then heated. The resulting solution was refluxed for 6 hours, partly cooled and concentrated on a rotary evaporator to give a yellow-brown solid (96.8 g). This material was crystallized from 125 ml of ethanol to give 58.1 g (66%) of a pale yellow solid, melting point 98°-100°. After recrystallization of 55.0 g of this material from 100 ml of ethanol, the nearly colorless solid weighed 52.7 g (63%).

Melting point: 101°-103°;

$R_f$ 0.56 (18:1:1-CH$_2$Cl$_2$-methanol-acetic acid).

Thin layer chromatography showed that none of the faster-moving erythro isomer was present in this material. Tanabe (European Patent Application No. 0154838) reports a melting point of 99.5° to 102.5° C.

Analysis calculated for C$_{18}$H$_{21}$NO$_5$S: C,59.48; H,5.83; N,3.85; S,8.82. Found: C,59.41; H,5.86; N,3.75; S,8.81.

1-B. (+)-Threo-2-hydroxy-3-(2-amino-5-methoxyphenylthio)-3-(4-methoxyphenyl)propionic acid, methyl ester, salt with D-(−) tartaric acid A mixture of 5.45 g (15.0 mmol) of compound 1−A and 2.50 g of 16.7 mmol) of D−(−) tartaric acid was treated with 50 ml of hot 95% ethanol. The suspension was heated to obtain a clear solution and then cooled in a water bath to obtain a crystalline product. After standing at room temperature for 3 hours, the solid was filtered, washed with 95% ethanol and dried to give 3.73 g (97%) of nearly colorless solid.

Melting point 167°-168° (foaming).

[α]$_D$+130° (c, 1% methanol). After recrystallization from 40 ml of 95% ethanol in the same manner, the colorless solid weighed 3.20 g (83%).

Melting point 168°-169° (foaming).

[α]$_D$+140° (c, 1% methanol). Recrystallization did not change the melting point or [α]$_D$ value.

Analysis calculated for C$_{18}$H$_{21}$NO$_5$S.C$_4$H$_6$O$_6$: C, 51.45; H, 5.30; N, 2.73; S, 6.24. Found: C, 51.35; H, 5.15; N, 2.85; S, 6.24.

EXAMPLE 2

(+)-Threo-3-hydroxy-3-(2-amino-5-methoxyphenylthio)-3-(4-methoxyphenyl) propionic acid To a stirred solution of 4.0 g (100 mmol) of sodium hydroxide in 80 ml of water (under nitrogen) was added 8.00 g (15.6 mmol) of Example 1, followed by 80 ml of methanol. The solid rapidly dissolved and thin layer chromatography indicated the hydrolysis was almost complete in a few minutes. After 1 hour, the material was transferred to a beaker, diluted with 120 ml of water, cooled and stirred during the portionwise addition of 80 ml of 1.0 N hydrochloric acid to give a heavy precipitate of Example 2. After cooling for two hours, the mixture was filtered and dried to give 5.35 g (98%) of colorless solid.

Melting point 188°-189° (dec); [α]$_D$+286° (c, 1% dimethylformamide).

$R_f$ 0.42 (8:1:1-methylene chloride-methanol-acetic acid).

Analysis calculated for C$_{17}$H$_{19}$NO$_5$S.0.1H$_2$O: C, 58.14; H, 5.51; N, 3.99; S, 9.13 Found: C, 57.94; H, 5.37; N, 3.86; S, 8.87.

EXAMPLE 3

(+)-Cis-2,3-dihydro-3-hydroxy-8-methoxy-2-(4-methoxyphenyl)-1,5-benzothiazepin-4(5H)-one A stirred solution of 5.25 g (10.2 mmol) of Example 2 in 150 ml of dimethylformamide was treated with a solution of 3.40 g (17.8 mmol) of ethyl-3-(3-dimethylamino)propyl carbodiimide, hydrochloride in 20 ml of water (one portion). The pH of the solution was maintained at pH 4.5 to 5.0 by dropwise addition of 1.0 N HCl (required about 10 drops). Thin layer chromatography indicated the cyclization was essentially complete in three minutes. After stirring for 50 minutes, the solution was poured into 800 ml of water-ice to give a heavy precipitate. The mixture was allowed to cool for 4 hours, filtered and washed with water and allowed to dry overnight. This colorless product weighed 4.87 g (98%).

Melting point 190°-191°.

[α]$_D$ value was +95.0 (c, 1% in methanol).

NMR spectra, using the Eu. shift reagent, showed that none of the (−) isomer was present in this material.

Analysis calculated for C$_{17}$H$_{17}$NO$_4$S: C,61.61; H,5.17; N,4.23; S,9.67 Found: C,61.37; H,5.16; N,4.22; S,9.66.

EXAMPLE 4

[2S-[2α,3α,5(R*)]]-5-[[1-[(1,1-Dimethylethoxy)carbonyl]-2-pyrrolidinyl]methyl]-2,3-dihydro-3-hydroxy-8-methoxy-2-(4-methoxyphenyl)-1,5-benzothiazepin-4(5H)-one 4-A. S-1-(t-butoxycarbonyl)-2-pyrrolidinemethanol (S)-(+)-2-Pyrrolidinemethanol (15 g, 148.3 mmol) and Di-t-butyl dicarbonate (40 g, 178 mmol) in methylene chloride (500 ml) were stirred at room temperature for 5 hours. The solvent was evaporated at reduced pressure and the crude product converted to compound 4-A without further purification.

4-B. S-1-(t-butoxycarbonyl)-2-[(4-methoxyphenylsulfonyloxy)-methyl]-pyrrolidine

To compound 4-A (20.6 g, 102.4 mmol) in pyridine (100 ml) at room temperature under argon was added with stirring p-toluenesulfonyl chloride (23.4 g, 122.8 mmol). After 5 hours, additional p-toluenesulfonyl chloride (9.8 g, 51.2 mmol) was added. After a total of 23 hours stirring, the reaction mixture was diluted with ethyl acetate and washed with saturated aqueous $CuSO_4$ solution (three times). The organic layer was dried ($MgSO_4$), filtered and concentrated. The yellow liquid was chromatographed on a silica gel column and eluted with 10 to 30% ethyl acetate-hexane to give compound 4-B (32.1 g, 88%) as a viscous colorless liquid.

4-C. [2S-[2α,3α,5(R*)]]-5-[[1-[(1,1-Dimethyl-ethoxy)carbonyl]-2-pyrrolidinyl]methyl]-2,3-dihydro-3-hydroxy-8-methoxy-2-(4-methoxyphenyl)-1,5-benzothiazepin-4(5H)-one A stirred mixture of Example 3, (1.50 g, 4.5 mmol), compound 4-B (3.00 g, 8.4 mmol), dimethylformamide (30 ml) and cesium carbonate (3.0 g, 9.2 mmol), under argon, was heated in a bath at about 50° to 60° for 24 hours. The mixture was cooled, poured onto 200 ml of ice-water to give a heavy precipitate. After standing in the ice-bath for 1 hour, the colorless solid was filtered and dried. This material (2.74 g) was purified by chromatography on 60 g of Baker's silica gel (60–200 mesh) and 60:1 methylene chloride-methanol as the eluant. The fractions containing only product were combined and concentrated to give 1.23 g (52%) of a colorless, free-flowing product.

Melting point 75°–80°.

$R_f$ 0.24 (1:1 ethyl acetate-hexane;

$[α]_D + 119°$ (c, 1% methanol). Additional product was recovered from the earlier fractions.

EXAMPLE 5

[2S-[2α,3α,5(R*)]]-3-(Acetyloxy)-5-[[1-[(1,1-dimethylethoxy)carbonyl-2-pyrrolidinylmethyl]-2,3-dihydro-8-methoxy-2-(4-benzothiazepin-4(5H)-one Example 4 (1.23 g, 2.4 mmol), acetic anhydride (1.25 g, 12.2 mmol) and 4-dimethylaminopyridine (0.64 g, 5.2 mmol) in methylene chloride (25 ml) under argon was stirred for 24 hours at room temperature. The solvent was removed on a rotary evaporator and the residual oil (3.47 g) was purified by chromatography using 35 g of Baker's silica gel (60–200 mesh) and 60:1 methylene chloride-methanol as the eluant. The fractions containing the product were combined and evaporated to give 1.17 g (89%) of a colorless solid.

Melting point 65°–70°.

$R_f$ 0.39 (1:1 ethyl acetate-hexane).

$[α]_D + 98.5°$ (c, 1% methanol).

EXAMPLE 6

[2S-[2α,3α,5(R*)]]-3-(Acetyloxy)-2,3-dihydro-8-methoxy-2-(4-methoxyphenyl)-5-(2-pyrrolidinylmethyl)-1-benzothiazepin-4(5H)-one, monohydrochloride A stirred solution of Example 5 (1.13 g, 2.03 mmol) in 10 ml of methylene chloride under argon was gradually treated with 10 ml of trifluoroacetic acid. After 30 minutes at room temperature, the solvents were removed on a rotary evaporator and the pale orange residual oil (2.53 g) was dissolved in 40 ml of ethyl acetate, cooled and treated with saturated potassium bicarbonate to neutralize the residual acid. The aqueous phase was discarded and the organic layer was extracted with 5 ml of saturated potassium bicarbonate, dried over magnesium sulfate, filtered and the solvent evaporated to give 0.98 g of a pale yellow solid. The latter was dissolved in 10 ml of acetonitrile and the solution was treated with 0.40 ml of 5.1 N HCl in ethanol. This solution was diluted to 50 ml with ether to give a crystallization solid. After standing overnight in the cold, the product was filtered and dried; weight 0.87 g (80%).

Melting point 226°–228° (dec.).

After crystallization from 150 ml of acetonitrile, the colorless product weighed 0.78 g.

Melting point 228°–230° (dec).

$R_f$ 0.48 (8:1:1 methylene chloride-methanol-acetic acid);

$[α]_D + 49.4°$ (c, 1% methanol).

Analysis calculated for $C_{24}H_{28}N_2O_5S \cdot HCl \cdot 0.75$ $CH_3CN \cdot 0.75$ $H_2O$: C,57.01; H,6.14; N,7.17; Cl,6.60; S,5.97. Found: C,56.90; H,5.87; N,7.20; Cl,6.55; S,5.78.

The acetonitrile was removed from this material by dissolving in distilled water and freeze-drying to give a colorless solid. Melting point 137–142°.

$[α]_D + 54.7°$ (c,1% methanol).

Analysis calculated for $C_{24}H_{28}O_5S \cdot HCl \cdot 1.5$ $H_2O$ C,55.42; H,6.20; N,5.39; Cl,6.81; S,6.17. Found: C,55.61; H,5.85; N,5.37; Cl,7.21; S,6.29.

EXAMPLE 7

(2S-cis-5-[(4,5-Dihydro-1H-imidazol-2-yl)methyl]-2,3-dihydro-3-hydroxy-8-methoxy-2-(4-methoxy-phenyl)-1,5-benzothiazepin-4(5H)-one, hydrochloride A stirred solution of 3.12 g (9.41 mmol) of Example 3 in 25 mL of dimethylformamide (under a stream of argon) was treated with 0.38 g (9.4 mmol) of sodium hydride (60%). Hydrogen was rapidly evolved from this mixture. After stirring for 30 minutes at room temperature, the solution was treated with 1.70 g (14.3 mmol) of 2-(chloromethyl) imidazoline (freshly-prepared from the hydrochloride salt). The reaction was almost complete in 10 minutes. After stirring for 2 hours, the mixture was poured onto 150 mL of ice-water to give a heavy colorless precipitate. The cool mixture was filtered, washed with cold water and air-dried to give a tan solid. This material was dissolved in 40 mL of methylene chloride, dried over magnesium sulfate, filtered, and the solvent evaporated to give 3.44 g (88%) of a free-flowing solid. Part of this material (1.00 g) was purified by chromatography using 35 g of Baker's silica gel (60–200 mesh) and 8:2:1 (dichloromethane:methanol:acetic acid) as the solvent. The fractions containing the product were combined and evaporated to give a residual foam. The latter was dissolved in 30 mL of acetonitrile, filtered with a small amount of silica gel and the filtrate was treated with 0.47 mL of 5.1 N hydrochloric acid in ethanol. This solution was concentrated on a rotary evaporation to give 0.75 g of a granular solid, melting point 150°–155° (foaming);

$[α]_D + 74.1°$ (c, 1% methanol). Crystallization of 0.52 g of this material from 3 mL of ethanol gave 0.39 g (43%) of colorless product.

Melting point 150°–155° (sintering at 100°)

$[α]_D + 74.3°$ (c, 1% methanol).

Analysis calculated for $C_{21}H_{23}N_3O_4S \cdot HCl \cdot 1.5CH_3C-H_2OH$: C,55.53; H,6.41; N,8.10; Cl,6.83; S,6.18. Found: C,55.61; H,6.03; N,8.03; N,8.30; Cl,6.43; S,5.95.

In order to remove the ethanol from this product, 0.36 g of material was dissolved in 5 mL of distilled water. After freeze-drying, the colorless solid weighed 0.35 g (43%) melting point 179°–182° (sintering at 155°);

$[α]_D + 80.5°$ (c, 1% methanol);

$R_f = 0.65$ (18:1:1 methylene chloride-methanol-acetic acid).

Analysis calculated for $C_{21}H_{23}N_3O_4S \cdot HCl \cdot 1.25\ H_2O$: C,55.39; H,5.65; N,8.90; Cl,7.51; S,6.79. Found: C,55.34; H,5.41; N,8.58; Cl,7.65; S,6.91.

What is claimed is:

1. A process for preparing the (+)-threo isomer by resolution of its racemic mixture of a substrate of the formula

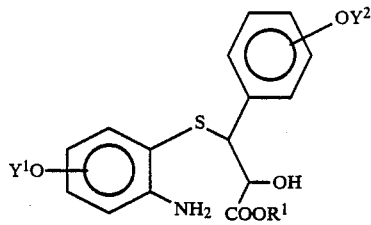

wherein $Y^1$ and $Y^2$ are each independently lower alkyl and $R^1$ is hydrogen or lower alkyl, which comprises:
   (a) treating the racemic threo mixture of the substrate with a chiral acid in an organic solvent; and
   (b) isolating the (+)-threo isomer.

2. The process of claim 1, further comprising: hydrolyzing the resolved substrate with an aqueous alkali hydroxide to yield a (+)-threo product of the formula

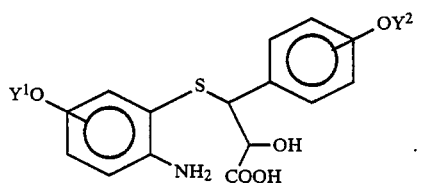

3. The process of claim 2, further comprising: reacting the (+)-threo product of claim 2 with an aqueous solution of ethyl-3-(3-dimethylamino)propyl carbodiimide, hydrochloride to yield a (+)-cis product of the formula

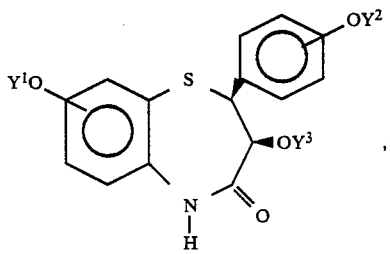

wherein $Y^3$ is hydrogen.

4. The process of claim 3, further comprising:
   (a) treating the (+)-cis product of claim 3 with a base; and
   (b) reacting the so-treated product of claim 3 with a reactant of the formula $R^2$-L or a protected form thereof, to yield a (+)-cis product of the formula

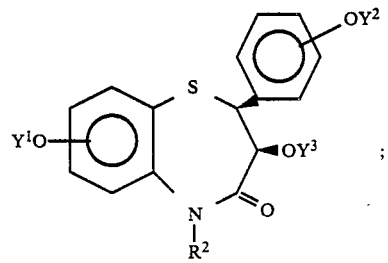

wherein $R^2$ is

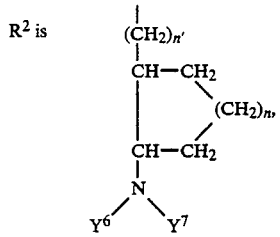

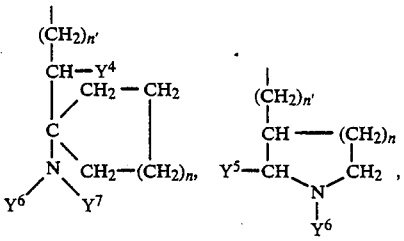

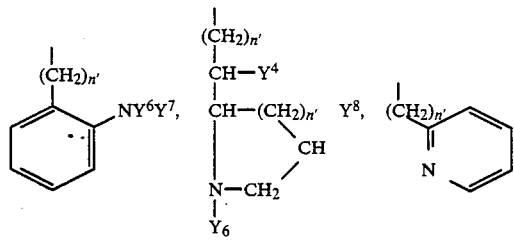

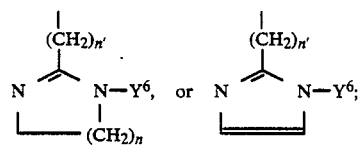

$Y^3$ is hydrogen;

$Y^4$ and $Y^5$ are each independently hydrogen, alkyl, aryl or arylalkyl, provided that when both are present they are not both hydrogen, and provided further that when both are attached to the same carbon atom neither is hydrogen;

$Y^6$ and $Y^7$ are each independently hydrogen, alkyl, cycloalkyl or arylalkyl; or $Y^6$ and $Y^7$ together with the nitrogen atom to which they are attached are azetidinyl, pyrrolidinyl, piperidinyl, or morpholinyl;

$Y^8$ is hydrogen, hydroxy, alkoxy, aryloxy or arylalkoxy;

n is 0, 1, 2, or 3;

n' is 0, 1, 2, or 3; and

L is a leaving group.

5. The process of claim 3, further comprising acylating the product of claim 3 to yield a new product wherein Y³ is

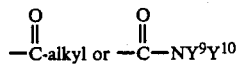

and Y⁹ and Y¹⁰ are each independently hydrogen, alkyl, aryl, or heteroaryl, or Y⁹ and Y¹⁰ together with the nitrogen atom to which they are attached are pyrrolidinyl, piperidinyl, or morpholinyl.

6. The process of claim 4, further comprising acylating the product to yield a new product wherein y³ is

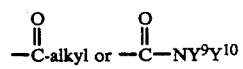

and Y⁹ and Y¹⁰ are each independently hydrogen, alkyl, aryl, or heteroaryl, or Y⁹ and Y¹⁰ together with the nitrogen atom to which they are attached are pyrrolidinyl, piperidinyl, or morpholinyl.

7. The process of claims 1 to 6, wherein Y¹ and Y² are methyl.

8. The process of claims 1 to 6, wherein R¹ is methyl.

9. The process of claims 1 to 6, wherein —OY¹ and —OY² are attached so that the substrate has the formula

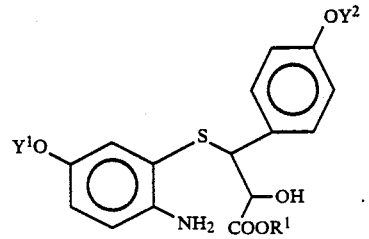

10. The process of claims 5 or 6, wherein Y³ is acetyl.

11. The process of claims 4 or 6 wherein R² is

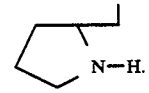

12. The process of claims 4 or 6 wherein R₂ is

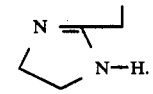

13. The process of claims 1 to 6, wherein the organic solvent is ethanol.

14. The process of claims 1 to 6, wherein the chiral acid is D-(—)-tartaric acid.

* * * * *